(12) United States Patent
Iordanov et al.

(10) Patent No.: US 8,840,839 B2
(45) Date of Patent: Sep. 23, 2014

(54) HYDROGEL BASED DEVICE FOR DETECTING AN ENVIRONMENTAL STATE

(75) Inventors: Ventzeslav Petrov Iordanov, Eindhoven (NL); Hendrika Cecilia Krijnsen, Eindhoven (NL); Michel Paul Barbara Van Bruggen, Eindhoven (NL); Anna-Maria Janner, Eindhoven (NL); Ralph Kurt, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1199 days.

(21) Appl. No.: 12/593,305

(22) PCT Filed: Apr. 2, 2008

(86) PCT No.: PCT/IB2008/051224
§ 371 (c)(1),
(2), (4) Date: Sep. 28, 2009

(87) PCT Pub. No.: WO2008/122926
PCT Pub. Date: Oct. 16, 2008

(65) Prior Publication Data
US 2010/0114072 A1    May 6, 2010

(30) Foreign Application Priority Data

Apr. 5, 2007 (EP) .................................... 07105697

(51) Int. Cl.
*G01N 21/00* (2006.01)
*A61B 5/00* (2006.01)
*A61B 5/1459* (2006.01)

(52) U.S. Cl.
CPC ............. *A61B 5/1459* (2013.01); *A61B 5/4839* (2013.01); *A61B 5/0008* (2013.01); *A61B 5/0031* (2013.01)
USPC ....................................... 422/82.05; 356/436

(58) Field of Classification Search
USPC ............ 600/32, 573–584, 322–341; 356/436; 435/14; 436/63–70; 422/62–98, 422/400–430, 50–54, 500–570
See application file for complete search history.

(56) References Cited

U.S. PATENT DOCUMENTS 5,028,394 A    7/1991  Lowell et al.
6,475,750 B1 *  11/2002  Han et al. ......................... 435/14
(Continued)

FOREIGN PATENT DOCUMENTS

WO    0116575 A1    3/2001

OTHER PUBLICATIONS

Baldi et al: "A Hydrogel-Actuated Environmentally Sensitive Microvalve for Active Flow Control"; Journal of Microelectromechanical Systems, vol. 12, No. 5, Oct. 2003, pp. 613-621.

*Primary Examiner* — Nicholas Lucchesi
*Assistant Examiner* — Weng Lee

(57) ABSTRACT

A transducer device for detecting an environmental state within a biological material including a channel comprising a fluid, a hydrogel material, which is adapted to change its volume when getting into contact with an environmental material and/or when detecting an environmental change, and which is mechanically coupled to the channel such that the volume of the channel changes when the volume of the hydrogel material changes. The transducer device further includes a sensor, which is adapted to generate a signal upon detection of the change of a physical property of the fluid that is induced by the volume change of the channel. By applying the transducer device, an accurate monitoring of physiological parameters, for which the hydrogel material is sensitive is possible. It is also possible to apply the transducer device outside of the bodily lumen, for example to monitor the blood of a patient outside the bodily lumen.

12 Claims, 3 Drawing Sheets

(56) References Cited

U.S. PATENT DOCUMENTS

| | | |
|---|---|---|
| 6,935,165 B2 | 8/2005 | Bashir et al. |
| 2002/0155425 A1* | 10/2002 | Han et al. ............... 435/4 |
| 2002/0197456 A1 | 12/2002 | Pope |
| 2003/0112443 A1* | 6/2003 | Hjelme et al. ............... 356/480 |
| 2004/0248326 A1 | 12/2004 | Ziaie et al. |
| 2005/0054111 A1 | 3/2005 | Breimesser et al. |
| 2006/0102483 A1 | 5/2006 | Chuang et al. |

\* cited by examiner

HYDROGEL BASED DEVICE FOR DETECTING AN ENVIRONMENTAL STATE

FIELD OF THE INVENTION

The invention relates to a transducer device for detecting an environmental state, in particular for detecting an environmental state within a biological material.

Further, the present invention relates to a medical system comprising the described transducer device.

Furthermore, the present invention relates to a method for detecting an environmental state, in particular for detecting an environmental state within a biological material, by means of a transducer device.

BACKGROUND OF THE INVENTION

Highly sensitive, selective, and robust sensors capable of monitoring small volumes of body fluids are one of the key components for developing responsive drug delivery systems. Protein engineering and molecular biology have facilitated the molecular design of bio-reagents, which are used as the sensing elements in various systems that offer high selectivity, good response times, and low detection limits. In addition, bio sensors have been developed for physiologically relevant molecules, such as neurotransmitters and hormones.

Stimuli-sensitive hydrogels have found applications in actuators, sensors, drug delivery and bio separations. These materials are able to respond reversibly to an external stimulus that causes a distinct measurable effect on the physical properties of the material. Hydrogels are known to be sensitive to pH, ion concentration, temperature, solvent composition and electric potential. The hydrogels can be also designed to swell upon presence of a target molecule. They can be constructed in a way that the magnitude of swelling can be proportional to the concentration of ligands being present.

Application of a stimuli-sensitive hydrogel in an implantable microscale system for drug delivery is known from US 2004/024832 in which a fluid flow through a channel is regulated by the hydrogel in response to a predetermined stimulus in a medium contacting the hydrogel. The reversible volume change leads to a reversible gating of the channel allowing the microscale component to act as an active microvalve. In this way the hydrogel-actuated microvalve mechanically couples the volume change of the hydrogel in response to a predetermined chemical compound to the opening and closing of the channel by a membrane.

A disadvantage of the known system is that is only capable of drug delivery and that is not capable of accurate monitoring of physiological parameters outside of and/or within a bodily lumen.

SUMMARY OF THE INVENTION

It is an object of the invention to provide a transducer device for detecting an environmental state or a change in the environmental state, in particular for detecting an environmental state within a biological material, which is capable of accurate monitoring of physiological parameters outside of and/or within a bodily lumen. The invention is defined by the independent claims. Advantageous embodiments are defined by the dependent claims.

This object is achieved by the transducer device according to the invention, wherein the transducer device comprises a channel comprising a fluid, a hydrogel material, which is adapted to change its volume when getting into contact with an environmental material and/or when detecting an environmental change, and which is mechanically coupled to the channel such that the volume of the channel changes when the volume of the hydrogel material changes, and a sensor, which is adapted to generate a signal upon detection of the change in a physical property of the fluid that is induced by the volume change of the channel.

The hydrogel material is adapted to be sensitive to the environmental state and/or a change of the environmental state, which may be a physical, chemical or biological property, condition or object. A change in the environment of the hydrogel material, such as for example the temperature or pH, and/or a contact with an environmental material, such as for example a specific molecule, induces a change of the volume of the hydrogel material. In response to this volume change of the hydrogel material, the volume of the channel changes as well, because of the specific mechanical contact between the hydrogel material and the channel. The volume change of the channel will affect a physical property of the fluid in the channel, such as for example pressure, flow or transparency. The sensor detects the change of the physical property of the fluid and, as a result, generates a signal. In this way the transducer device generates a signal in the case that the hydrogel material reacts to an environmental change and/or gets into contact with an environmental material, for both of which the hydrogel material is sensitive. The signal generated by the sensor of the transducer device according to the invention in fact is a monitor for the environmental change and/or environmental material of the transducer device. The signal may be used for different purposes, such as for example for triggering an event, for example a drug release or storage of data in a memory device for later access by a medical specialist. By applying the transducer device according to the invention within a bodily lumen, an accurate monitoring of physiological parameters, for which the hydrogel material is sensitive, within the bodily lumen is possible. It is also possible to apply the transducer device outside of the bodily lumen, for example to monitor the blood of a patient outside the bodily lumen. The fluid may be the material that is to be monitored or a carrier fluid the properties of which are influenced by the environmental state and/or environmental material.

The object of the invention is also achieved by a method for detecting an environmental state, in particular for detecting an environmental state within a biological material, by means of a transducer device comprising a hydrogel material and a channel comprising a fluid, the method comprising the steps of:

getting the transducer device into contact with the biological material, such that a hydrogel material changes its volume such that the volume of the channel changes, generating a signal upon detection of a change of a physical property of the fluid that is induced by the change of the volume of the channel.

The object is also achieved by a medical system comprising the transducer device according to the invention, and a drug release device, which is coupled to the transducer device and which is adapted to release a certain amount of drug when being triggered by the signal of the transducer device. In this way the monitoring function of the transducer device according to the invention is advantageously used to trigger the drug release.

In an embodiment of the transducer device according to the invention, the sensor is adapted to measure a change in the pressure and/or the flow of the fluid in the channel. The volume change of the hydrogel material may induce a change in, for example, flow and pressure of the fluid in the channel. The amount of change in flow and pressure is measured by the sensor and this change can be used to calculate the volume change of the hydrogel material, which is used, via the known properties of the hydrogel material, to extract the amount of change of the physical properties of the environment and/or the environmental material of the transducer device. From this an appropriate signal is generated by the sensor.

In another embodiment of the transducer device according to the invention, the transducer device further comprises a light source, which is adapted to radiate light into the channel, and in which the sensor is adapted to measure a change in the optical properties of the fluid in the channel. The volume change of the channel influences the optical properties of the fluid, such as for example the absorption of light because the path length of the light in the fluid changes upon the change in volume of the hydrogel material.

In an embodiment of the transducer device according to the invention, the transducer device comprises a substrate in which the sensor is integrated, and on which substrate the channel and the hydrogel material are formed. In this way a compact and small-sized transducer device is obtained, which, for example, can be advantageously applied within a bodily lumen. In an advantageous embodiment the light source is integrated in the substrate.

In an embodiment of the transducer device according to the invention, the transducer device further comprises an electronic circuit in electrical contact with the sensor. In this way the functionality of the transducer device is enhanced. For example, the electronic circuit comprises a storage device for storing the signals generated by the sensor.

In an embodiment of the transducer device according to the invention, the transducer device further comprises a transmitter unit, which is adapted to communicate with an external receiving unit. In this way the transducer device can, for example, by applied within a bodily lumen without requiring wiring for control of the transducer device or for receiving the signal of the sensor.

BRIEF DESCRIPTION OF THE DRAWINGS

These and other aspects of the invention will be further elucidated and described with reference to the drawings, in which.

The Figures are not drawn to scale. In general, identical components are denoted by the same reference numerals in the Figures.

DETAILED DESCRIPTION OF EMBODIMENTS

Figure 1A:
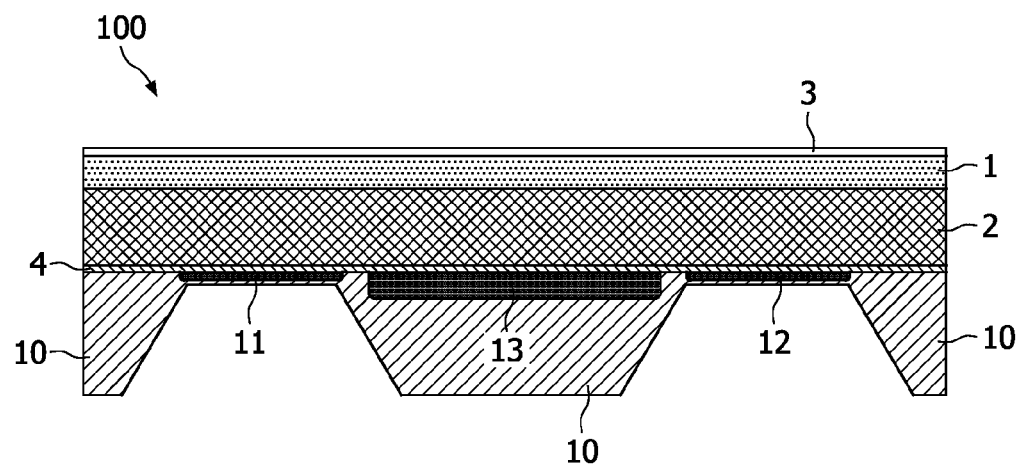
FIG. 1a is a cross-sectional view of an embodiment of the transducer device according to the invention.

Stimuli-sensitive hydrogel materials have applications in actuators, sensors, drug delivery, bioseparations and biomedicine. These materials are able to respond reversibly to an external stimulus that causes a distinct measurable effect on the properties of the material. Hydrogel materials are known to be sensitive to pH, ion concentration, temperature, solvent composition and electric potential. These parameters cause a change in phase, shape, mechanics, refractive index, recognition or permeation rates that subsequently can be reversed to return the material to its original state. Stimuli-sensitive hydrogel materials have also been integrated with enzymes, protein mimics, and antibodies to design controllable actuators. These hydrogel materials have been shown to swell on addition of a target molecule. The amount of swelling of these hydrogel materials was attributed to changes in non-covalent interactions within the polymer network. The hydrogel materials can be also designed to swell upon presence of a target molecule. They can even be constructed in a way that the magnitude of swelling can be proportional to the concentration of target molecule present. Huge swelling ratios can be obtained, the materials are, for example, very sensitive to even small changes in pH. A typical pH sensitive hydrogel material is polyacrylic acid (PAA) and a typical temperature sensitive hydrogel material is N-isopropylacrylamide (NPA). Some stimuli-responsive hydrogel materials additionally undergo very abrupt changes in optical properties in response to external stimuli such as temperature. An example of this effect is known as lower critical solution temperature. In fact some hydrogel materials undergo a very sharp phase transition when increasing the temperature and change from an optically transparent material into a scattering material. The fact that the lower critical solution temperature of these hydrogel materials can be adjusted to near human body temperature (37° C.) by copolymerization and using additives further makes them viable for in vivo applications. Furthermore, the use of water-based materials slows down the encapsulation process of a foreign body by the human immune system, which makes hydrogel materials extremely attractive as a base for implantable long lasting chemo-physical sensors. Hydrogel-based transducers therefore will lead to long lasting implantable sensing systems enabling accurate monitoring of physiological parameters outside of and/or within the human/animal body. The proposed transducer device makes use of the response of the hydrogel material to an environmental change (for example pH, temperature) or a specific molecule. In order to become sensitive to the presence of a specific molecule (analyte) the hydrogel should be "tailored" with specific "analyte-analyte binding molecules" complexes, for example antigen as analyte and an antibody as analyte binding molecule or carbohydrates as analyte and Lectins as analyte binding molecule.

Figure 1B:
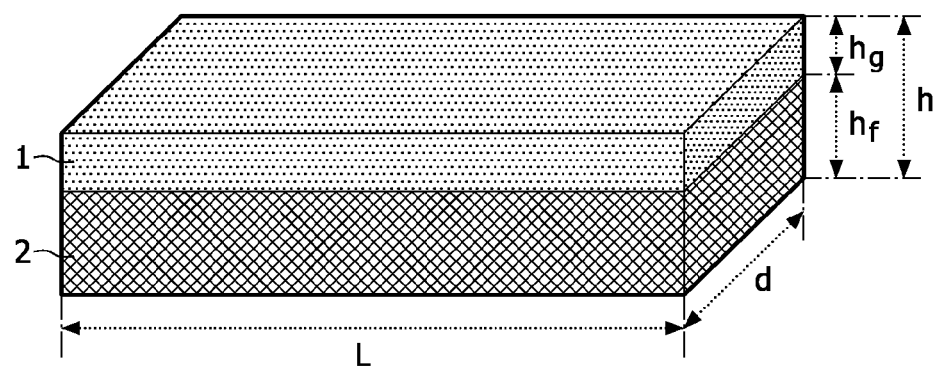
FIG. 1b is a perspective view of a part of the transducer device shown in FIG. 1b.

FIG. 1a shows a schematic cross-section of an embodiment of the transducer device according to the invention and FIG. 1b shows a perspective view of a part of the transducer device according to the invention. The transducer device 100 is integrated in and on a substrate 10, which is, for example, made of silicon material. A pressure sensor 11 and a flow sensor 12 are formed in the substrate 10 and are isolated from a channel 2 by an isolation layer 4, for example silicon dioxide. The sensors 11 and 12 are electrically connected to an electronic circuit 13 that is also integrated in the substrate 10. The electronic circuit 13 is, for example, adapted to receive signals from the sensors 11 and 12 and to calculate from these signals combined with other required data the amount of environmental change or the amount of environmental material. The channel 2 comprises a fluid, such as for example blood. Alternatively, the fluid may be a carrier fluid which properties are changed by the environmental state or the environmental material. A hydrogel material layer 1 is extending over the channel 2 and is covered by a protective layer 3, which is, for example, made of glass, silicon oxide, silicon, silicon nitride.

The swelling of the hydrogel material layer 1, under the assumption it occurs only in a direction perpendicular to the surface of the pressure sensor 11 and the flow sensor 12, can be expressed with:

$$S = \frac{V_2 - V_1}{V_1} \times 100\% = \frac{h_g^* - h_g}{h_g} \times 100\% = \frac{\Delta h_g}{h_g} \times 100\% \quad [1]$$

where:

$V_1$ and $V_2$ is the volume of the hydrogel material 1 in "dry" and "swollen" form respectively [m³];

$h_g$ and $h_g^*$ is the height of the hydrogel material 1 in "dry" and "swollen" form respectively [m]; and $\Delta h_g$ is the height difference between the "dry" and "swollen" form of the hydrogel material 1 [m].

The hydrogel height $h_g$ in Equation 1 can be calculated using the Hagen-Poiseuille formula for calculating the pressure drop (P) of a fluid, in laminar flow, through a, in this case, rectangular shaped channel 2:

$$P = \frac{\eta L \phi}{A^2} c_{PA} = \frac{\eta L v}{A} c_{PA}, \quad [2]$$

where:

$\phi$ is the volumetric flow velocity in the channel 2 [m³·s⁻¹];
v is the linear flow velocity in the channel 2 [m·s⁻¹];
$\eta$ is the liquid viscosity of the fluid [Pa·s];
L is the length of the channel 2 [m];
P is the pressure drop in the channel 2 [Pa];
A is the cross-section area of the channel 2 [m²]: $A = dh_f$;
d is the width of the channel 2 [m];
$h_f$ is the height of the fluid in the channel 2 [m]; and
$c_{PA}$ is a dimensionless parameter dependent on the shape of the channel 2.

In the case of a rectangular shaped channel 2, $c_{PA}$ is defined by:

$$c_{PA} = \frac{8(d + h_f)^2}{dh_f}, \quad [3]$$

The specific case of an initially square shaped channel 2 ($d = h_f$) leads to:

$$c_{PA} = \frac{8(2h_f)^2}{h_f^2} = 32, \quad [4]$$

From which it follows that:

$$P = \frac{32 \eta L v}{h_f^2} \Rightarrow h_f = \sqrt{\frac{32 \eta L v}{P}} \Rightarrow h_g = h - 4\sqrt{\frac{2 \eta L v}{P}}, \quad [5]$$

where:
h is the total height in the channel 2 [m].

Upon swelling, the hydrogel material 1 changes the shape of the channel 2, thereby reducing the dimensions of the channel 2, and consequently introducing either a change in the pressure of the fluid in the channel 2 (constant flow) or a change in the flow of the fluid in the channel 2 (constant pressure). By measuring the flow velocity and the pressure after swelling of the hydrogel material 1 in the channel 2 one can calculate the height difference between the "dry" and "swollen" form of the hydrogel material 1 $\Delta h_g$ using the Hagen-Poiseuille formula for calculating the pressure drop (P) of a fluid, in laminar flow, through a rectangular channel 2:

$$P_S = 8\eta L v_S \left(\frac{1}{d} + \frac{1}{h_f^S}\right)^2 \quad [6]$$

where:
$v_S$ is the linear flow velocity in the channel after gel swelling [m·s⁻¹];
$P_S$ is the pressure drop in the channel after gel swelling [Pa]; and
$h_f^S$ is the fluid height in the channel after gel swelling [m].

From Equation 6 one can calculate the fluid height in the channel after swelling of the hydrogel material 1 and from there the hydrogel heights difference between the "dry" and "swollen" form $\Delta h_g$:

$$\Delta h_g = d \frac{1 \pm \sqrt{k}}{k - 1} - h_f, \text{ where } k = \frac{d^2 P_S}{8\eta L v_S}, \quad [7]$$

Although there are several different methods of measuring the flow of the fluid in the channel 22, for example mechanically, electrically, magnetically or optically, the most widely spread method is based on thermal sensors, because of their structural and electronic simplicity. Furthermore, they are compatible with the standard integration technologies such as CMOS (Complementary Metal Oxide Semiconductor) and/or bipolar technologies. One example of the differential temperature measurements principle is based on the use of p-type polysilicon-n-type polysilicon thermopiles with a heater in-between.

The fluidic flow is proportional to the square of the temperature difference on the two sides of the heater and as a result the fluidic flow can be calculated from the measured temperature difference.

The most widely spread integrated pressure sensors are based on piezo-resistive type transducers, realized using Micro-Electro Mechanical Systems (MEMS) technologies. They are compatible with the standard integration technologies (such as CMOS (Complementary Metal Oxide Semiconductor) and/or bipolar technologies. The piezo-resistive type pressure sensor consists of a semiconductor (silicon) substrate with a membrane formed by backside etching of the substrate. The front side of the chip comprises, for example, four p-type diffused piezo-resistors in a Wheatstone bridge configuration. The resistors are located on the membrane and metal tracks provide electrical connections. When a pressure is applied, the membrane will deflect and the piezo-resistors change thereby misbalancing the Wheatstone bridge and generating a voltage across the Wheatstone bridge that is proportional to the applied pressure. Thus, using the Wheatstone bridge configuration one can calculate the applied pressure by measuring the voltage across the Wheatstone bridge.

Figure 2A:
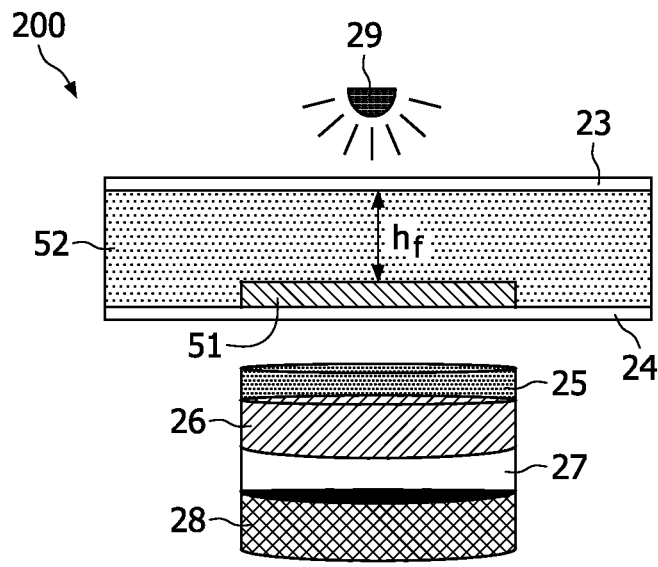
FIGS. 2a and 2b are cross-sectional views of a second embodiment of the transducer device according to the invention.
Figure 2B:
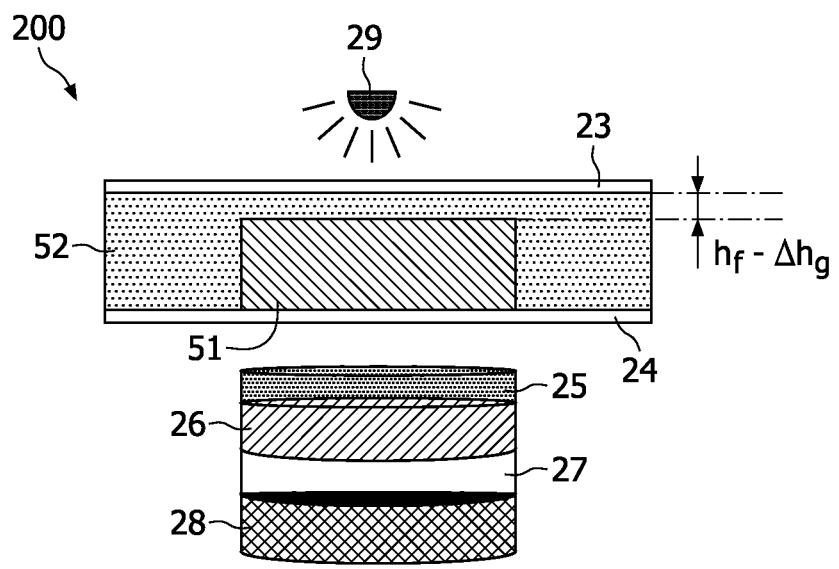

FIGS. 2a and 2b show another embodiment of a transducer device 200 according to the invention that is most suitable for in-vitro and ex-vivo applications, such as for example a catheter. The transducer device 200 is manufactured from discrete components and based on the reduced absorbance of light by a, for example, colored liquid, upon swelling of a hydrogel material 51, which in this case is a transparent hydrogel material 51. FIG. 2a shows the situation in which the hydrogel material 51 in a dry or non-swollen state, and FIG. 2b shows the situation in which the hydrogel material 51 is in a swollen state. The transducer device 200 comprises a channel 52 with the colored liquid, which comprises light absorbing particles. The transparent hydrogel material 51 is located in the channel 52 in a path of light originating from a light source 29. The channel 52 is protected by protective layers 23 and 24. The channel 52 may also comprise the environmental material that has to be detected, such as for example a molecule. In response to an environmental change, such as for example the temperature, or the presence of a specific molecule, the volume of the hydrogel material 51 increases, thereby reducing the height of the channel 52 at the location of the hydrogel material 51 and displacing the colored liquid. This results in a reduced absorbance of light in the colored liquid, because the path length of light in the colored liquid is reduced. The light that passes through the colored liquid in the channel 52 and the hydrogel material 51 is detected by an optical sensor 25, such as for example a photodetector, that is located in the path of light. In case of a volume increase of the hydrogel material 51, less light will be absorbed by the colored liquid and more light will be detected by the optical sensor 25. The optical sensor 25 generates a signal that is dependent on the amount of light detected. This signal is, for example, received by an electronic circuit 26, which is adapted to calculate from this signal the amount of environmental change or environmental material that is detected by the transducer device 200. This result can then be transmitted via a transmitter 27 to an external receiving unit (not shown) which can, for example store or present the results. The transducer device 200 further comprises a power source 28, for example a battery, to supply the required power the transducer device 200.

The hydrogel material 51 is in this case transparent for light, because it comprises, for example, mostly water. In order to achieve a sufficient transparency of the hydrogel material 51 after swelling no light absorbing molecules should be present in the hydrogel material 51. This can be obtained by tailoring the hydrogel material 51 in a way that its network does not allow particles with certain sizes or properties to enter.

Examples of a light absorbing molecule that can be used in the colored liquid are ATTO 580Q and ATTO 612Q (http://www.atto-tec.com).

In order to calculate the change in the signal upon swelling of the hydrogel material 51 and the height difference between the "dry" and "swollen" form of the hydrogel material 51 $\Delta h_g$, first the molar extinction coefficient $\epsilon_k$ of the colored liquid is converted into an absorption coefficient $\alpha$ by:

$$\alpha = \frac{2.303\varepsilon_k c_k}{m_W}, [cm^{-1}] \quad [8]$$

where:
$\epsilon_k$ is the molar extinction coefficient of the colored liquid [mol$^{-1}$·liter·cm$^{-1}$];
$c_k$ is the absorbing particle concentration in the colored liquid [g·liter$^{-1}$]; and
$m_W$ is the molecular weight of the absorbing particle in the colored liquid [g·mol$^{-1}$].

The height difference between the "dry" and "swollen" form of the hydrogel material 51 $\Delta h_g$ is extracted from the ratio between the corresponding signals:

$$\frac{S_D}{S_S} = \frac{S_0 \exp(-\alpha h_f)}{S_0 \exp(-\alpha h_f^S)} = $$

$$\frac{\exp(-\alpha h_f)}{\exp(-\alpha(h_f - \Delta h_g))} = \exp(-\alpha \Delta h_g) \Rightarrow \Delta h_g = \frac{1}{\alpha} \ln\left(\frac{S_S}{S_D}\right) \quad [9]$$

where:
$S_D$ is the signal obtained when the hydrogel material 51 is in its "dry" form;
$S_S$ is the signal obtained when the hydrogel material 51 is in its "swollen" form; and
$S_0$ is the signal obtained when there is no fluid in the channel 52.

As a practical example the colored liquid comprises an absorption molecules concentration of 500 mg·liter$^{-1}$ and the absorption coefficient $\alpha$=148 cm$^{-1}$, the optical source 29 has a luminous intensity of about 2500 mcd ($\approx$3.5 mW), the optical sensor 25 has a responsivity $\Re$ =0.45 A·W$^{-1}$ at a wavelength of 620 nm (absorption maximum of ATTO 612Q), and the height of the channel when the hydrogel material is in the "dry" state h$_f$=0.1 cm, from which the size of the minimal electrical current can be calculated, which results from the largest size of the channel 52 at the location of the hydrogel material 51, for example when the hydrogel material 51 is in its "dry" form, by using:

$$I_D = E_D \Re = E_0 \exp(-\alpha h_f) \Re \quad [10]$$

where:
$E_0$ is the luminous intensity of the optical source 29 [W];
$\alpha$ is the absorption coefficient of the colored liquid [cm$^{-1}$];
$h_f$ is the height of the channel when the hydrogel material is in the "dry" state [cm];
$\Re$ is the responsivity of the optical sensor 25 [A·W$^{-1}$]; and
$I_D$ electrical current generated by the optical sensor.

This results and electrical current of approximately ~0.6× 10$^{-9}$ A.

Figure 3A:
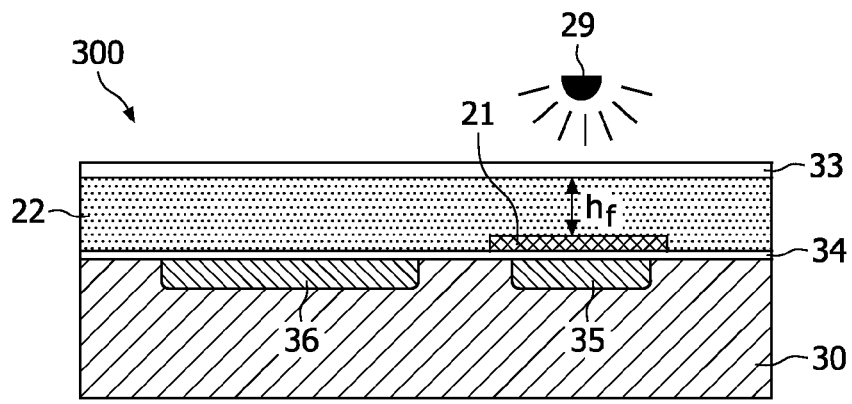
FIGS. 3a and 3b are cross-sectional views of a third embodiment of the transducer device according to the invention.
Figure 3B:
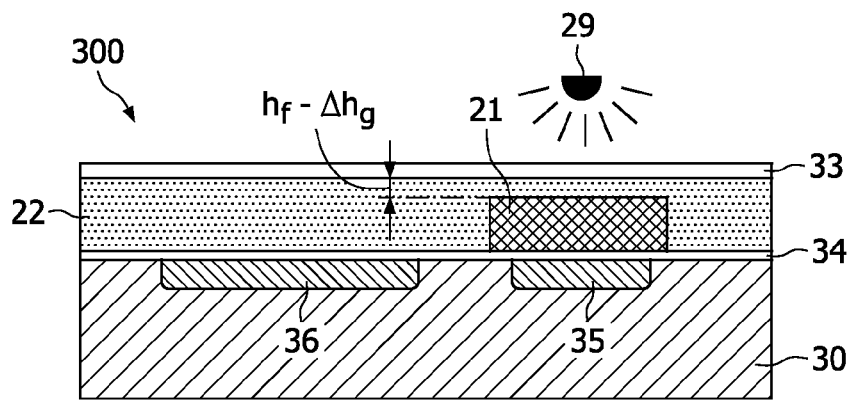

FIGS. 3a and 3b show another embodiment of a transducer device 300 according to the invention that is most suitable for in-vivo applications. The transducer device 300 is an integrated and miniaturized version of the transducer device 200 and is also based on the reduced absorbance of light by the, for example, colored liquid, upon swelling of a hydrogel material 21, which in this case is also transparent. FIG. 3a shows the situation in which the hydrogel material 21 is in a dry or non-swollen state, and FIG. 3b shows the situation in which the hydrogel material 21 is in a swollen state. The transducer device 200 comprises a channel 22 with the colored liquid, which comprises light absorbing particles. The transparent hydrogel material 21 is located in the channel 22 in a path of light originating from the light source 29. The channel 22 is protected by protective layers 33 and 34. The channel 22 may also comprise the environmental material that has to be detected, such as for example a molecule. In response to an environmental change, such as for example the temperature, or the presence of a specific molecule, the volume of the hydrogel material 21 increases, thereby reducing the height of the channel 22 at the location of the hydrogel material 21 and displacing the colored liquid. This results in a reduced absorbance of light in the colored liquid, because the path length of light in the colored liquid is reduced. The light that passes through the colored liquid in the channel 22 and the hydrogel material 21 is detected by an optical sensor 35 that is located in the path of light and is integrated in a substrate 30, which is for example of silicon material. In case of a volume increase of the hydrogel material 21, less light will be absorbed by the colored liquid and more light will be detected by the optical sensor 35. The optical sensor 35 generates a signal that is dependent on the amount of light detected. This signal is, for example, received by an electronic circuit 36, which is also integrated in the substrate 30 and which is adapted to calculate from this signal the amount of environmental change or environmental material that is detected by the transducer device 300. This result can then be transmitted via a transmitter (not shown) to an external receiving unit (not shown) which can, for example, store or present the results.

Figure 4:
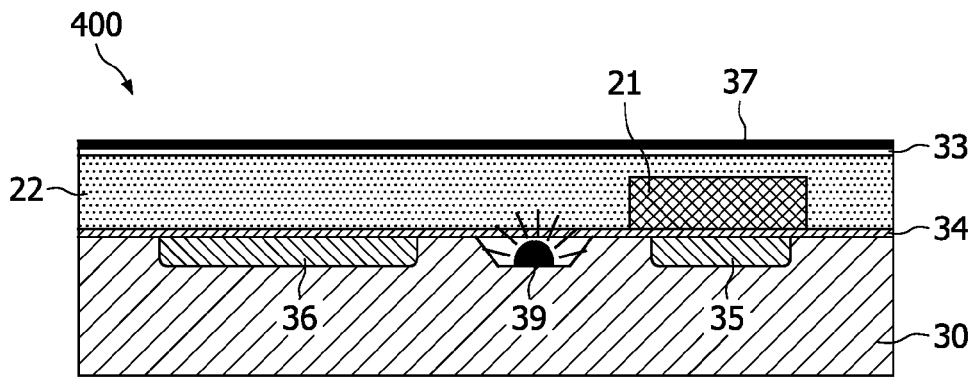
FIG. 4 is a cross-sectional view of a fourth embodiment of the transducer device according to the invention.

FIG. 4 shows another embodiment of a transducer device 400 according to the invention in which an optical source 39 is integrated in the same substrate 30 as the optical sensor 35 and the electronic circuit 36, thereby further miniaturizing the transducer device 400. In order to optimally detect the difference in the absorption pattern, the top surface of the channel 22 is covered with a reflective layer 37, comprising for example a metal, that reflects the irradiated light towards the optical sensor 35. The integration of all components in one substrate 30 makes the system more compact and therefore can be used in applications where miniature structures are required. Since the light travels twice trough the channel 22 the absorption will be twice as high compared to the transducer device 300. Therefore this configuration is suitable for systems with a small sized channel 22, for example with a diameter smaller than 0.5 mm.

The formation of the channel 2, 22 on the substrate 10,30 can be performed in the same process for manufacturing the integrated substrate by applying additional post-processing steps. For example, the channel 2, 22 can be formed in a layer of photoresists material, such as for example SU8 material, that is spun over the substrate 10,30, and subsequently patterned and developed. The channel 2, 22 can be also formed in silicon or silicon dioxide. The channel 2, 22 can alternatively be formed in a second substrate, for example silicon or glass, by known etching techniques, followed by bonding of the second substrate on the substrate 10,30 comprising the sensors. The hydrogel material 1, 21 can be brought into the channel 2, 22 and polymerized last or in the case of a second substrate prior to the bonding step.

To prepare the hydrogel material 1, 21 monomers are usually mixed with a solvent, for example water, buffer solution or methanol, typically in a 50/50 to 10/90 ratio. To form a chemically crosslinked hydrogel material a crosslinker is added, for example N,N-methylene bisacrylamide, n-(ethyleneglycol)diacrylate (n=4-10000), typically in a 1:10 to 1:1000 ratio with the monomer. Further a photo- or thermal initiator, possibly in combination with an accelerator, is added to initiate the polymerization. In case of a patterned hydrogel material, photo-polymerization is preferred. By tuning the content of the mixture in the appropriate way during polymerization, phase separation can be obtained to form a microporous hydrogel material 1,21. Important parameters for this are for example the solvent fraction and the crosslink density. The porosity of the hydrogel material 1, 21 might be tuned also by adding polyoxyethylene (100) stearyl ethers (e.g. Brij 700, an emulsion stabilizer).

In an example of manufacturing a pH sensitive hydrogel material a hydrogel mixture a 75% pH 7 buffer solution (Fluka) and 25% acrylic acid/PEGDA (n=10) 90:10 wt % is mixed in a 50:1 ratio with Irgacure 2959. The surface of the substrate 10,30, which is for example silicon, silicon dioxide and or silicon nitride, can be coated with an adhesion promotor, such as for example trimethoxy-silane methacrylate (A174). The substrate 10,30 is the first treated with UV ozone for approximately 10 minutes and subsequently the silane is applied by evaporation. This step can also be done locally by, for example, microcontact printing. Moreover surfaces for which no contact with the hydrogel is required can be coated with a fluorinated silane or by a plasma treatment, thereby realizing a non-wetting surface. The channel 2, 22 on the substrate 10,30 can be then filled with the hydrogel mixture. In order to polymerize the hydrogel material the cell is to be exposed for about 1 hour to UV light with an optical power of about 1 $mW\cdot cm^2$ in a nitrogen atmosphere. A higher light intensity will allow a shorter exposure time. In a preferred embodiment exposure of a special mask is applied. After rinsing with water, the response of the hydrogel material to pH changes.

The hydrogel material based transducer device 100,200, 300,400 are useful in general for monitoring and/or detection of molecules, substances, labels, drugs, or environmental changes for in-vivo and in-vitro application. When the diagnostic device is suitable for in vitro analysis of a fluid, the diagnostic device may further comprise an entry port and an outlet for the fluid. The transducer device 100,200,300,400 can be used in evaluation of drug impact, new drug discovery and drug testing. Applications areas include also the fields of diagnostics, where the presence and amount of a specific bio-molecule has to be measured an/or continuously monitored. The transducer device 100,200,300,400 can be applied to humans as well as to animals.

In summary, the invention relates to transducer device for detecting an environmental state or a change in the environmental state, in particular for detecting an environmental state within a biological material. The transducer device comprises a channel comprising a fluid, a hydrogel material, which is adapted to change its volume when getting into contact with an environmental material and/or when detecting an environmental change, and which is mechanically coupled to the channel such that the volume of the channel changes when the volume of the hydrogel material changes. The transducer devices further comprises a sensor, which is adapted to generate a signal upon detection of the change of a physical property of the fluid that is induced by the volume change of the channel. By applying the transducer device according to the invention within a bodily lumen, an accurate monitoring of physiological parameters, for which the hydrogel material is sensitive, within the bodily lumen is possible. It is also possible to apply the transducer device outside of the bodily lumen, for example to monitor the blood of a patient outside the bodily lumen.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of other elements or steps than those listed in a claim. The word "a" or "an" preceding an element does not exclude the presence of a plurality of such elements.

The invention claimed is:

1. A transducer device for detecting an environmental state within a biological material, the transducer device comprising:
   a channel comprising a liquid;
   a hydrogel material, adapted to change its volume when getting into contact with the biological material and/or when detecting a change in the environmental state of the biological material, and which is mechanically coupled to the channel such that the volume of the channel changes when the volume of the hydrogel material changes;
   a light source adapted to radiate light into the channel; and a sensor adapted to generate a signal upon detection of the change in a physical property of the liquid that is induced by the volume change of the channel.

2. The transducer device as claimed in claim 1, wherein the sensor is adapted to measure a change in the pressure and/or the flow of the liquid in the channel.

3. The transducer device as claimed in claim 1, wherein the sensor is adapted to measure a change in the optical properties of the liquid in the channel.

4. The transducer device as claimed in claim 1, comprising a substrate in which the sensor is integrated, and on which substrate the channel and the hydrogel material are formed.

5. The transducer device as claimed in claim 1, wherein the light source is integrated in the substrate.

6. The transducer device as claimed in claim 1, further comprising an electronic circuit in electrical contact with the sensor.

7. The transducer device as claimed in claim 1, further comprising a transmitter unit, which is adapted to communicate with an external receiving unit.

8. A method for detecting an environmental state within a biological material, by means of a transducer device comprising a hydrogel material and a channel comprising a liquid, the method comprising acts of:
getting the transducer device into contact with the biological material, such that a hydrogel material changes its volume such that the volume of the channel changes;
radiating light from a light source into the channel; and
generating a signal upon detection of a change in a physical property of the liquid that is induced by the change of the volume of the channel.

9. A method for detecting an environmental state within a biological material, by means of a transducer device comprising a hydrogel material and a channel comprising a liquid, the method comprising acts of:
radiating light from a light source into the channel;
getting the transducer device into contact with the biological material, such that a hydrogel material changes its volume such that the volume of the channel changes;
generating a signal upon detection of the change of the optical properties of the liquid that is induced by the change of the volume of the channel.

10. A medical system comprising:
a transducer device for detecting an environmental state within a biological material, the transducer device comprising:
a channel comprising a liquid;
a hydrogel material, adapted to change its volume when getting into contact with the biological material and/or when detecting a change in the environmental state of the biological material, and which is mechanically coupled to the channel such that the volume of the channel changes when the volume of the hydrogel material changes;
a light source adapted to radiate light into the channel;
a sensor, which is adapted to generate a signal upon detection of the change in a physical property of the liquid that is induced by the volume change of the channel, and a drug release device, coupled to the transducer device and adapted to release a certain amount of drug when being triggered by the signal of the transducer device.

11. The transducer device according to claim 1, wherein the transducer device is adapted as a diagnostic device.

12. The transducer device according to claim 11, wherein the diagnostic device is adapted for in vitro analysis of the liquid and further comprises an entry port and an outlet for the liquid.

* * * * *